United States Patent
Stark (10) Patent No.: US 6,288,398 B1
(45) Date of Patent: Sep. 11, 2001

(54) SUPPORT STRUCTURE FOR MEDICAL DIAGNOSTIC EQUIPMENT

(75) Inventor: Iain Stark, Nepean (CA)

(73) Assignee: IS² Research Inc., Nepean (CA)

( * ) Notice: Subject to any disclaimer, the term of this patent is extended or adjusted under 35 U.S.C. 154(b) by 0 days.

(21) Appl. No.: 09/127,989

(22) Filed: Aug. 3, 1998

(30) Foreign Application Priority Data

Aug. 1, 1997 (CA) .................................................. 2212196

(51) Int. Cl.⁷ .................................................. G01T 1/166
(52) U.S. Cl. .............................. 250/363.08; 250/363.03; 250/363.05
(58) Field of Search ........................ 250/363.08, 363.05, 250/363.03

(56) References Cited

U.S. PATENT DOCUMENTS

| | | |
|---|---|---|
| 3,765,549 | 10/1973 | Jones . |
| 4,064,441 | 12/1977 | Casale . |
| 4,216,381 | 8/1980 | Lange . |
| 4,223,222 | 9/1980 | Gray et al. . |
| 4,459,485 * | 7/1984 | Span .................................. 250/363.05 |
| 4,651,007 | 3/1987 | Perusek et al. . |
| 4,652,758 * | 3/1987 | Barfod .............................. 250/363.05 |
| 4,774,411 * | 9/1988 | Span .................................. 250/363.08 |
| 5,047,641 | 9/1991 | Besseling et al. . |
| 5,146,094 | 9/1992 | Stark . |
| 5,278,416 * | 1/1994 | Pierfitte ............................ 250/363.08 |
| 5,349,190 * | 9/1994 | Hines et al. ....................... 250/363.05 |
| 5,717,212 * | 2/1998 | Fulton et al. ...................... 250/363.05 |
| 5,866,906 * | 2/1999 | Jensen .............................. 250/363.05 |
| 5,998,792 * | 12/1999 | DiFilippo .......................... 250/363.05 |

FOREIGN PATENT DOCUMENTS 0 266 846 A2   5/1992   (EP) .

* cited by examiner

*Primary Examiner*—Constantine Hannaher
*Assistant Examiner*—Otilia Gabor
(74) *Attorney, Agent, or Firm*—Finnegan, Henderson, Farabow, Garrett & Dunner, L.L.P.

(57) ABSTRACT

A support structure for medical diagnostic equipment provides entirely independent motions on all axes of the detector and very precise and reproducible motions while allowing for static, linear and rotational imaging such as by a rotatable scintillation detector. The support structure includes a rotor or ring on which there are two arms on which the detector is mounted and a counterweight attached by links to the opposite end of the arms and on the opposite side of the rotor. The arms, on which the detector is rotatably mounted, are attached to the rotor by means of short, double pivoted links which allow the arms to move towards or away from the rotor and pivot with respect to the rotor. Two secondary arms are connected to the pivot point of the detector and to a track mounted on the rotor. The counterweight end of the primary arms, and hence the scintillation detector may be vertically displaced to a desired position without change in the distance from the rotor and without angular displacement of the plane of view.

26 Claims, 9 Drawing Sheets

SUPPORT STRUCTURE FOR MEDICAL DIAGNOSTIC EQUIPMENT

FIELD OF INVENTION

The present invention relates to a support structure for medical diagnostic equipment. More particularly, the present invention relates to a support structure for supporting and controlling the relative positions of a patient and a scintillation camera.

BACKGROUND OF THE INVENTION

In the human body, increased metabolic activity is associated with an increase in emitted radiation. In the field of nuclear medicine, increased metabolic activity within a patient is detected using a radiation detector such as a scintillation camera.

Scintillation cameras are well known in the art, and are used for medical diagnostics. A patient ingests, or inhales or is injected with a small quantity of a radioactive isotope. The radioactive isotope emits photons that are detected by a scintillation medium in the scintillation camera. The scintillation medium is commonly a sodium iodide crystal, BGO or other. The scintillation medium emits a small flash or scintillation of light, in response to stimulating radiation, such as from a patient. The intensity of the scintillation of light is proportional to the energy of the stimulating photon, such as a gamma photon. Note that the relationship between the intensity of the scintillation of light and the gamma photon is not entirely linear.

A conventional scintillation camera such as a gamma camera includes a detector which converts into electrical signals gamma rays emitted from a patient after radioisotope has been administered to the patient. The detector includes a scintillator and photomultiplier tubes. The gamma rays are directed to the scintillator which absorbs the radiation and produces, in response, a very small flash of light. An array of photodetectors, which are placed in optical communication with the scintillation crystal, converts these flashes into electrical signals which are subsequently processed. The processing enables the camera to produce an image of the distribution of the radioisotope within the patient.

Gamma radiation is emitted in all directions and it is necessary to collimate the radiation before the radiation impinges on the crystal scintillator. This is accomplished by a collimator which is a sheet of absorbing material, usually lead, perforated by relatively narrow channels. The collimator is detachably secured to the detector head, allowing the collimator to be changed to enable the detector head to be used with the different energies of isotope to suit particular characteristics of the patient study. A collimator may vary considerably in weight to match the isotope or study type.

Scintillation cameras are used to take four basic types of pictures: spot views, whole body views, partial whole body views, SPECT views, and whole body SPECT views.

A spot view is an image of a part of a patient. The area of the spot view is less than or equal to the size of the field of view of the gamma camera. In order to be able to achieve a full range of spot views, a gamma camera must be positionable at any location relative to a patient.

One type of whole body view is a series of spot views fitted together such that the whole body of the patient may be viewed at one time. Another type of whole body view is a continuous scan of the whole body of the patient. A partial whole body view is simply a whole body view that covers only part of the body of the patient. In order to be able to achieve a whole body view, a gamma camera must be positionable at any location relative to a patient in an automated sequence of views.

The acronym "SPECT" stands for single photon emission computerized tomography. A SPECT view is a series of slice-like images of the patient. The slice-like images are often, but not necessarily, transversely oriented with respect to the patient. Each slice-like image is made up of multiple views taken at different angles around the patient, the data from the various views being combined to form the slice-like image. In order to be able to achieve a SPECT view, a scintillation camera must be rotatable around a patient, with the direction of the detector head of the scintillation camera pointing in a series of known and precise directions such that reprojection of the data can be accurately undertaken.

A whole body SPECT view is a series of parallel slice-like images of a patient. Typically, a whole body SPECT view consists of equally spaced cross sections or vertical or horizontal longitudinal sections. A whole body SPECT view results from the simultaneous generation of whole body and SPECT image data. In order to be able to achieve a whole body SPECT view, a scintillation camera must be rotatable around a patient, with the direction of the detector head of the scintillation camera pointing in a series of known and precise directions such that reprojection of the data can be accurately undertaken.

Therefore, in order that the radiation detector be capable of achieving the above four basic views, the support structure for the radiation detector must be capable of positioning the radiation detector in any position relative to the patient. Furthermore, the support structure must be capable of moving the radiation detector relative to the patient in a controlled manner along any path.

In prior scintillation cameras, the vertical travel of a detector has been achieved by either counter-balancing the detector about a pivot or by a motor driven screw jack. This results in compromises in various areas of normal clinical operation including the possibility of varying the total weight of the detector, raising or lowering the detector and maintaining the focus of the collimator at the same point, the ability to perform complex motions around the patient and view the constant 'slice' of the patient and the precision and reproducibility of the motions.

While such scintillation camera systems have existed for about two decades now, performing to a greater or lesser degree satisfactorily, the advances in resolution in newer systems have created greater requirements in precision alignment between the detector and the patient or the patient support apparatus. One alternative system attempted to address this problem at the cost of great complexity. This has been particularly noticeable as nuclear camera systems have been used more and more for generating tomographic images by rotation of the detector about the patient, in addition to the more conventional static imaging. One such nuclear camera system capable of both whole body static imaging as well as emission computed tomography or ECT, is the Gemini system available from General Electric Corporation, Milwaukee, Wis., and described in U.S. Pat. No. 4,651,007 to Perusek et al.

In general, prior nuclear camera systems, regardless of whether they include ECT capability, feature a counter-balanced detector, with an inherent variable viewing point in the patient due to the radius from the pivot to the detector, a toe or forward projecting structure to stabilize the medical diagnostic positioner or the patient bed supported between two supports with the detector head mounted on a translatable support to traverse the patient length. The loss of resolution and contrast of the imaging device, the scintillation camera detector head, arises from variable viewing point in the patient due to the radius from the pivot to the detector and from a lack of precision alignment between the bed and detector head, particularly during rotation of the camera head.

Among the objects of the present invention are to provide: an improved support structure for medical diagnostic equipment, such as a nuclear camera; a support structure capable of supporting and positioning a nuclear camera in any position relative to a patient; a support structure capable of positioning a nuclear camera for spot views, whole body views, SPECT views, and whole body SPECT views; a support structure for a nuclear camera capable of accommodating a range of collimator weights; a support structure for a nuclear camera that is relatively inexpensive to manufacture.

SUMMARY OF THE INVENTION

The support structure of the present invention is designed to support and position a nuclear camera or other medical diagnostic equipment. The invention includes a stable base upon which an annular support rotates, advantageously in a vertical plane. An elongate support extends through the annular support. Attached to one end of the elongate support is a nuclear camera or other medical diagnostic device. Attached to the other end of the elongate support is a counter balance. A guide attaches the elongate support to the annular support, such that pivoting of the elongate support relative annular support results in movement of the camera end of the elongate support in a plane parallel to the plane of the annular support.

According to the invention, there is therefore provided a support structure for supporting and positioning a device relative to a patient, the support structure comprising: (a) a base; (b) a rotating support rotatable in a first plane relative to the base; (c) an elongate support pivotally attached to the rotating support at an angle to the first plane, the elongate support comprising a device end for supporting a device; and (d) a guide for restricting movement of the device end of the elongate support to a first plane fixed relative to the base.

According to the invention, there is therefore further provided a support structure for supporting and positioning a scintillation camera detector relative to a patient, the support structure comprising: (a) a base positionable on a ground surface and comprising a pair of spaced apart lower rollers; (b) a vertically oriented annular rotating support defining an orifice and a first vertical plane and being rotatable in the first vertical plane, the rotating support comprising: (i) an outside surface in rolling contact with the lower rollers; (ii) an inside surface for supporting a patient support; (iii) a front surface; and (iv) a rear surface; (c) an elongate support comprising a pair of spaced apart arms extending through the rotating support, the elongate support comprising: (i) a camera end for supporting a scintillation camera detector at a distance from the front surface of the rotating support; and (ii) a counter weight end for supporting a counter weight at a distance from the rear surface of the rotating support; (d) a guiding linkage connecting the rotating support to the elongate support such that pivotal movement of the elongate support relative to the rotating support results in movement of the camera end of the elongate support in a second vertical plane, the vertical plane being parallel to the first vertical plane; (e) a counter weight depending from the counter weight end of the elongate support; (f) an actuator for pivoting the elongate member relative to the annular support; and (g) a drive unit for rotating the annular support relative to the base.

Advantageously, the present invention provides: an improved support structure for medical diagnostic equipment, and particularly for imaging equipment, such as a nuclear camera; a support structure capable of supporting and positioning a nuclear camera in any position relative to a patient; a support structure capable of positioning a nuclear camera for spot views, whole body views, SPECT views, and whole body SPECT views; a support structure for a nuclear camera capable of accommodating a wide range of collimator weights; a support structure for a nuclear camera that is relatively inexpensive to manufacture.

Other advantages, objects and features of the present invention will be readily apparent to those skilled in the art from a review of the following detailed descriptions of preferred embodiments in conjunction with the accompanying drawings and claims.

BRIEF DESCRIPTION OF THE DRAWINGS

The embodiments of the invention will now be described with reference to the accompanying drawings, in which.

Similar references are used in different figures to denote similar components.

DETAILED DESCRIPTION OF THE INVENTION

Figure 1:
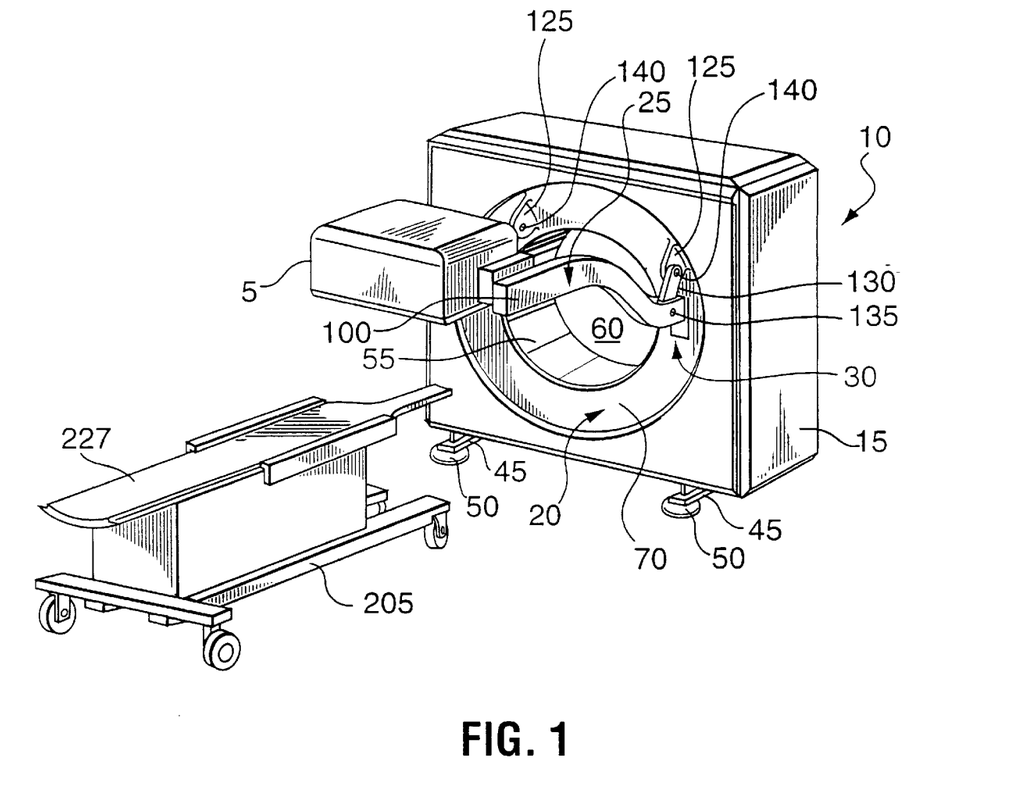
FIG. 1 is a perspective view of a scintillation camera showing only certain aspects of the invention, and specifically not illustrating the guide of the present invention.
Figure 2:
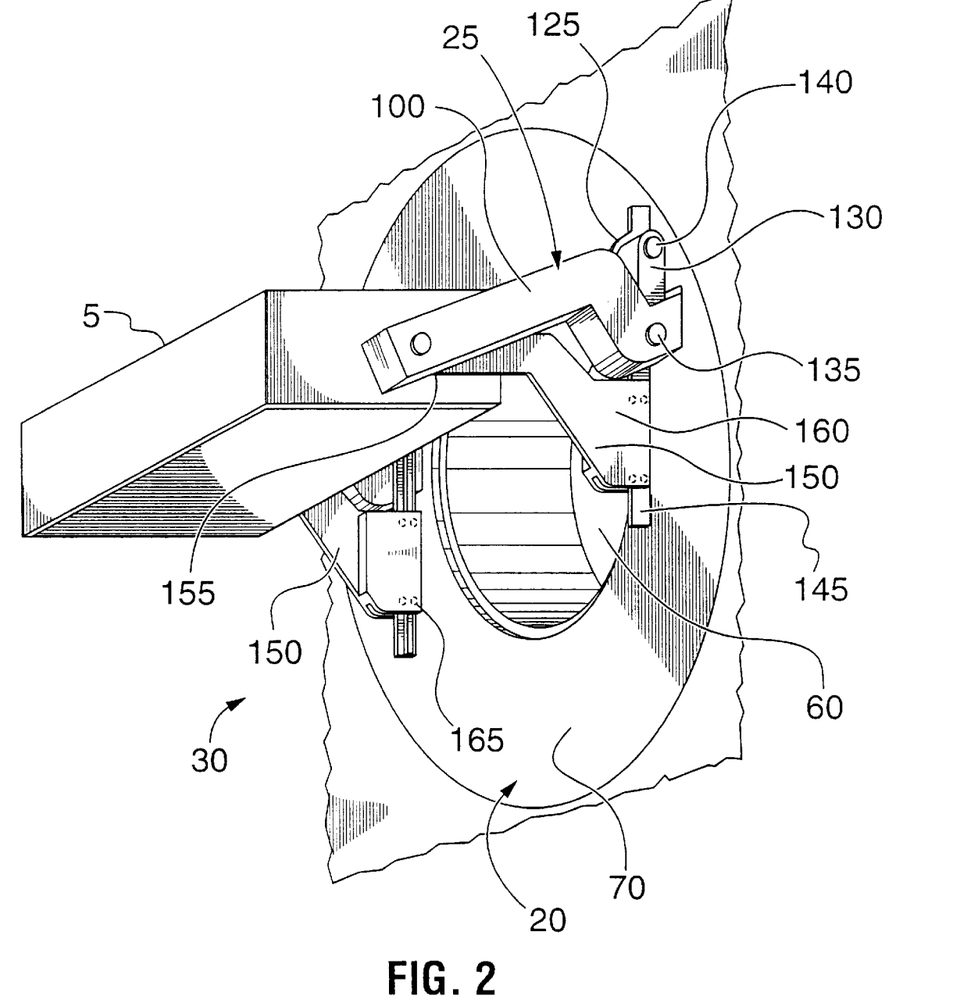
FIG. 2 is a partial perspective view of an embodiment of the invention, specifically illustrating the guide apparatus.
Figure 3:
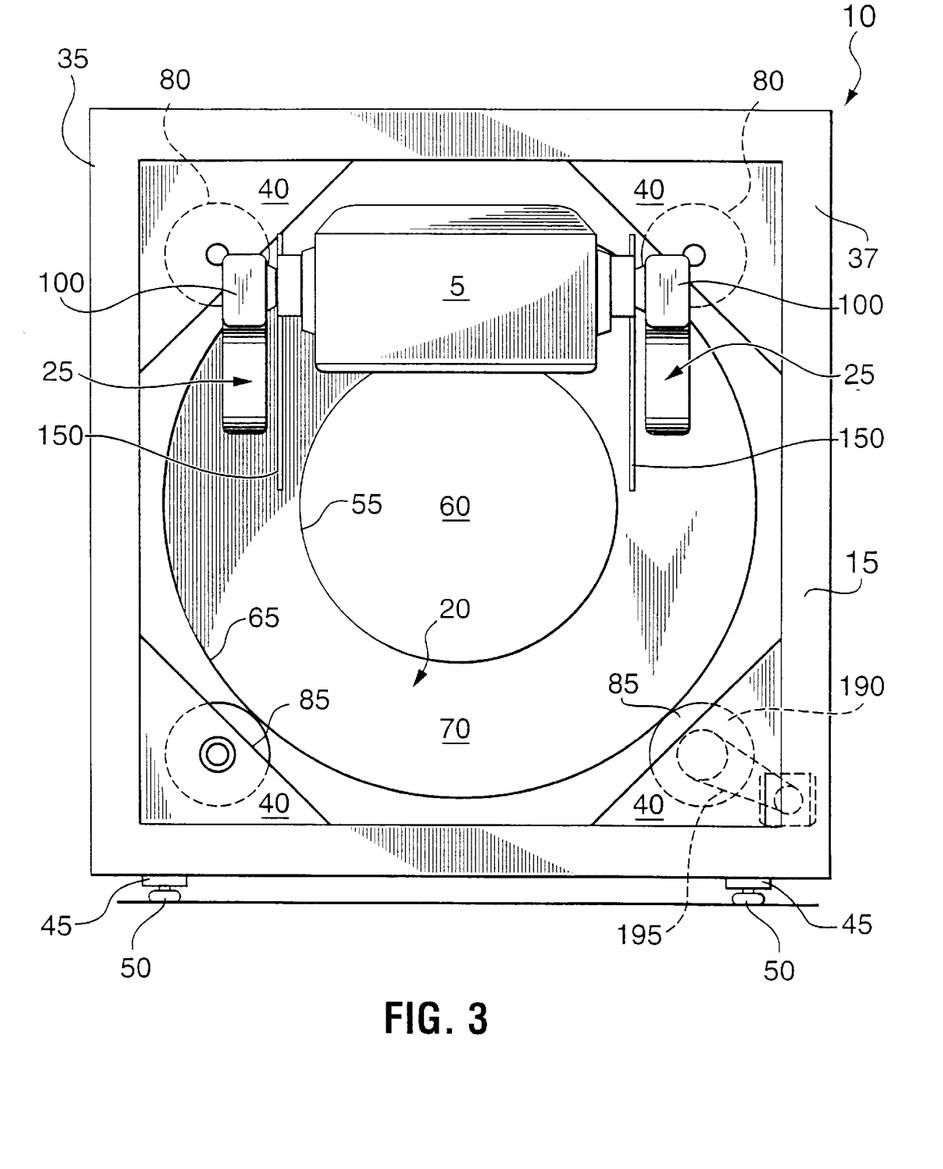
FIG. 3 is a front elevation view of an embodiment of the invention.
Figure 4:
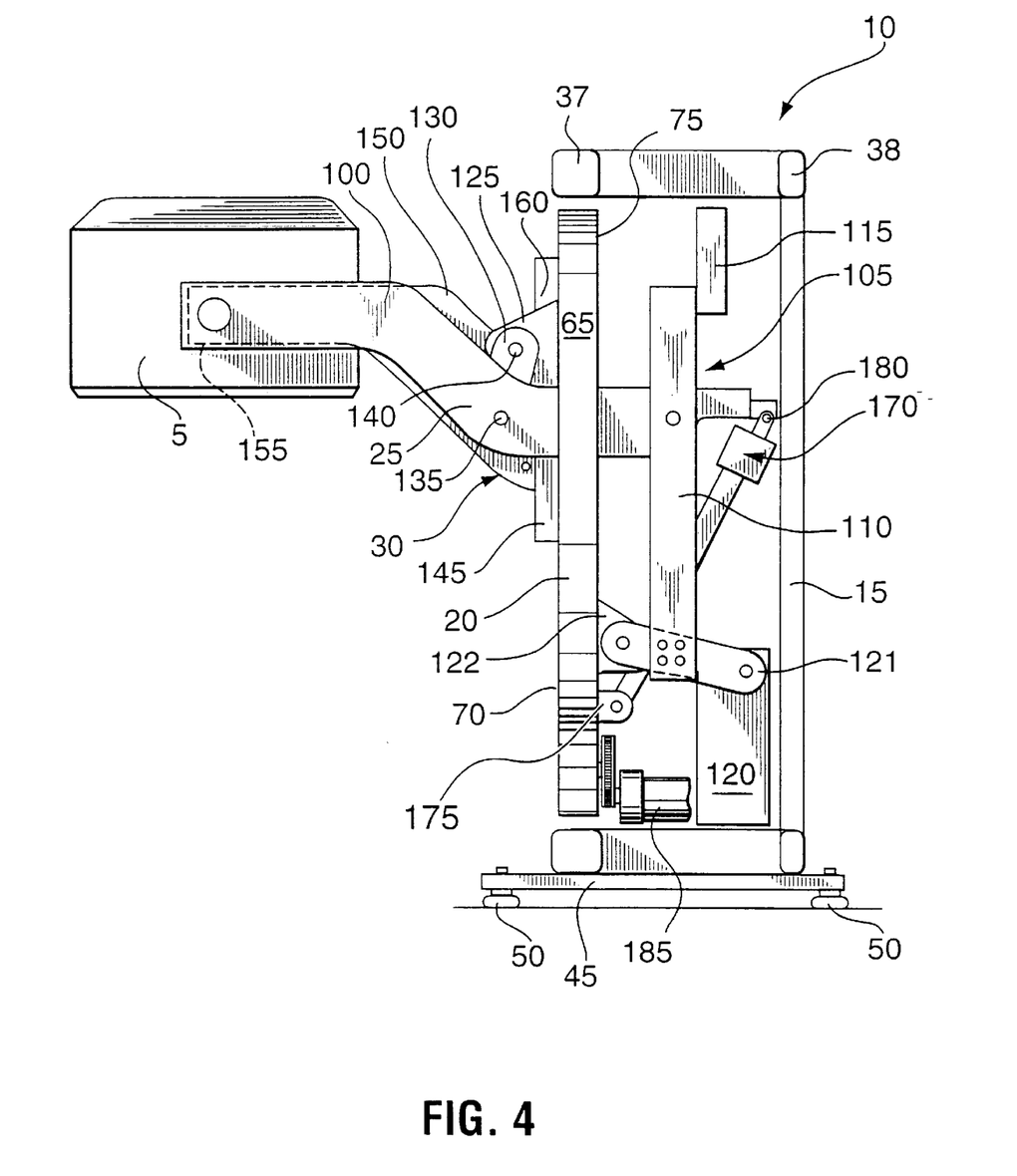
FIG. 4 is a side elevation view of an embodiment of the invention.
Figure 5:
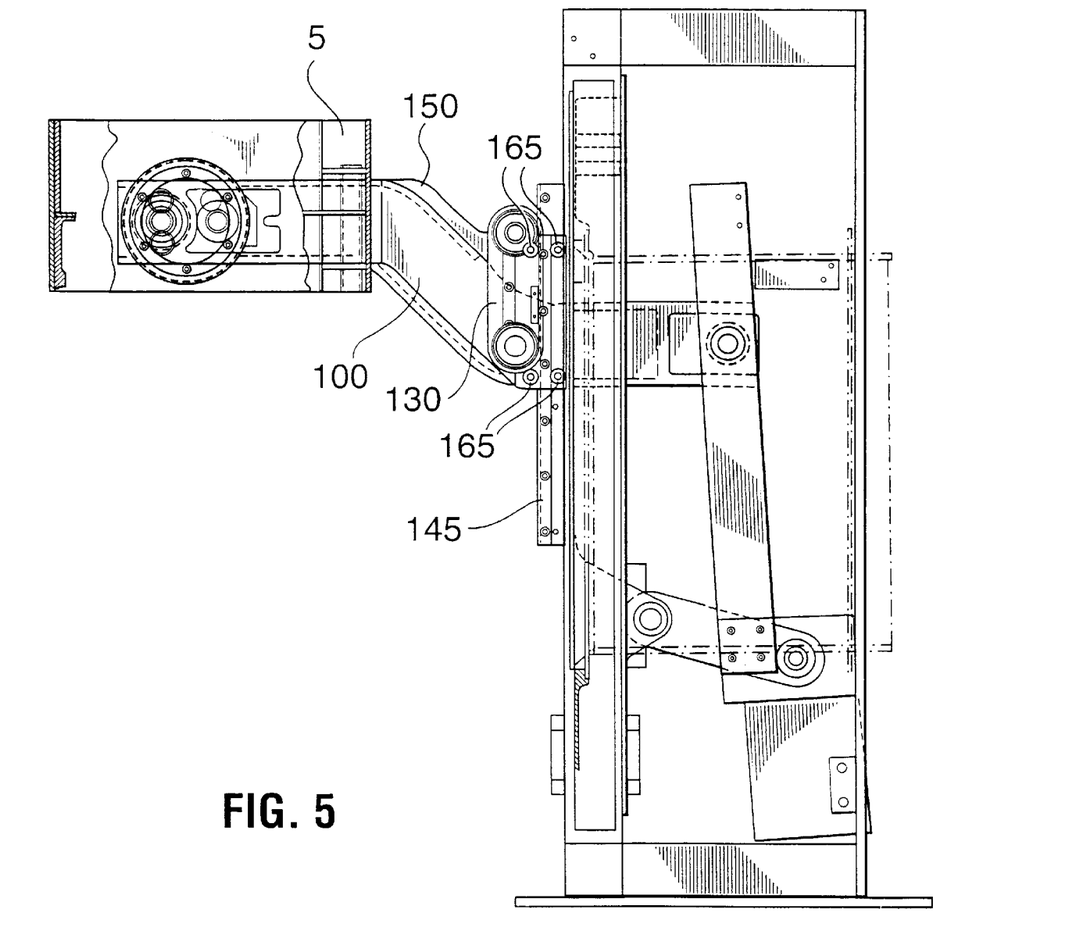
FIG. 5 is a side elevation view of an embodiment of the invention.
Figure 6:
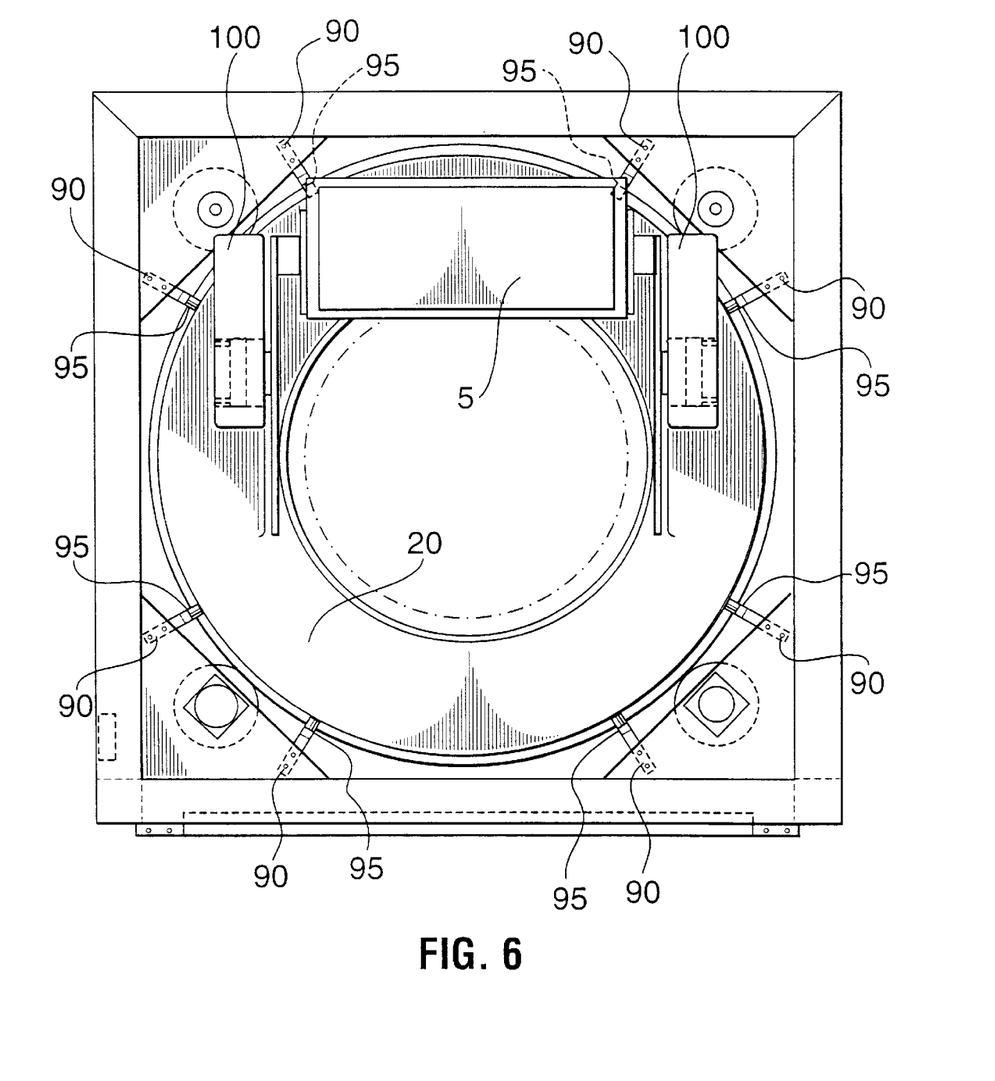
FIG. 6 is a front elevation view of an embodiment of the invention.
Figure 7:
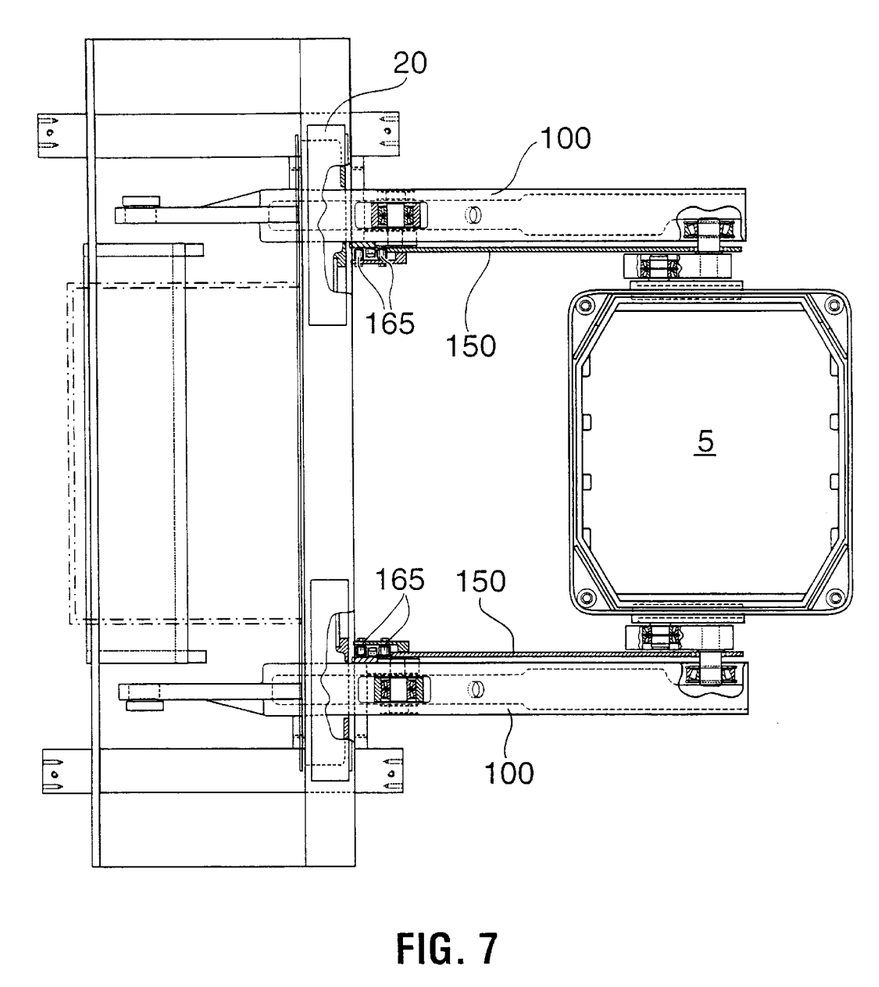
FIG. 7 is a top plan view of an embodiment of the invention.
Figure 8:
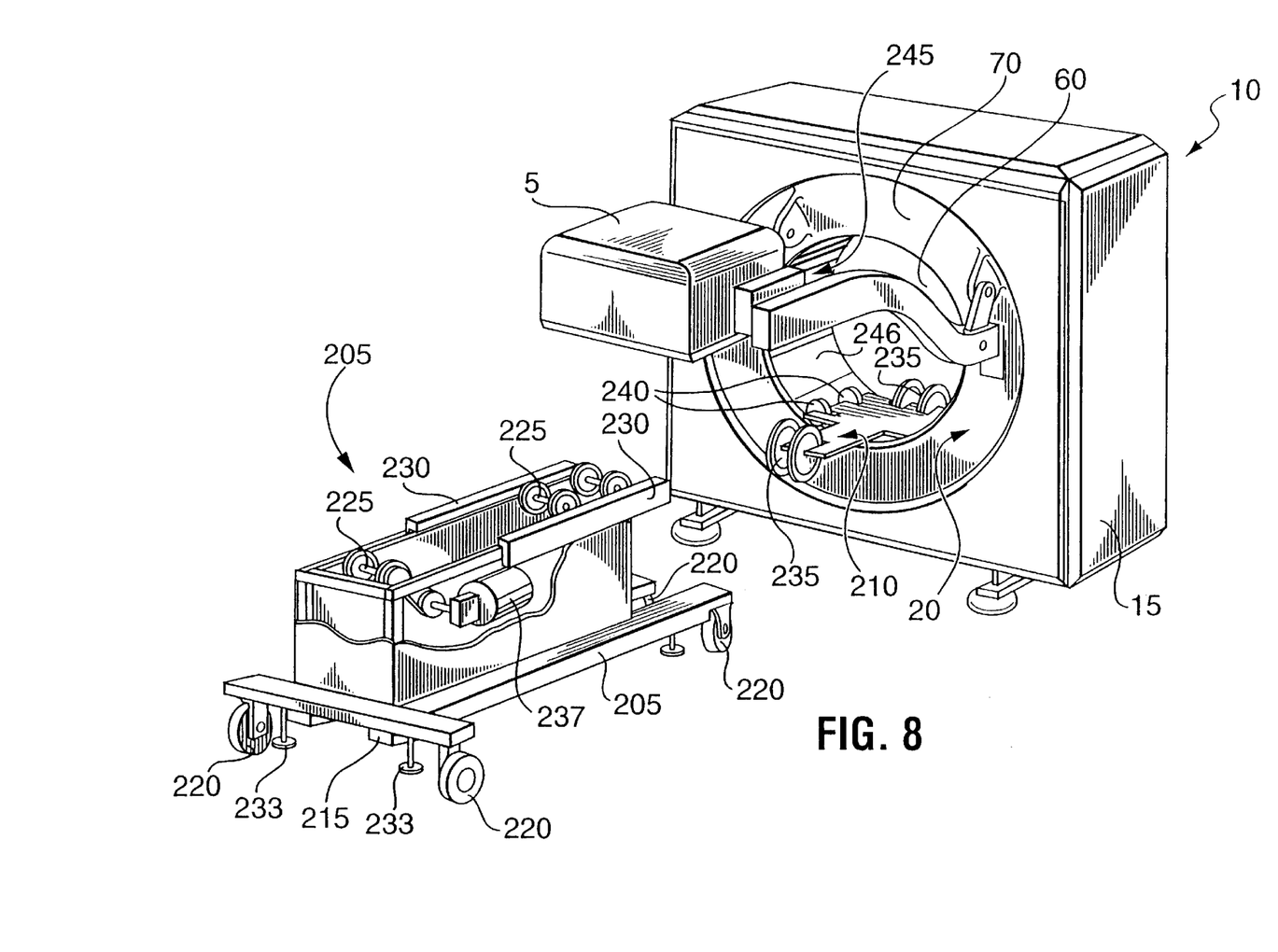
FIG. 8 is a perspective view of the scintillation camera of FIG. 1 but including a patient support apparatus with the stretcher removed.
Figure 9:
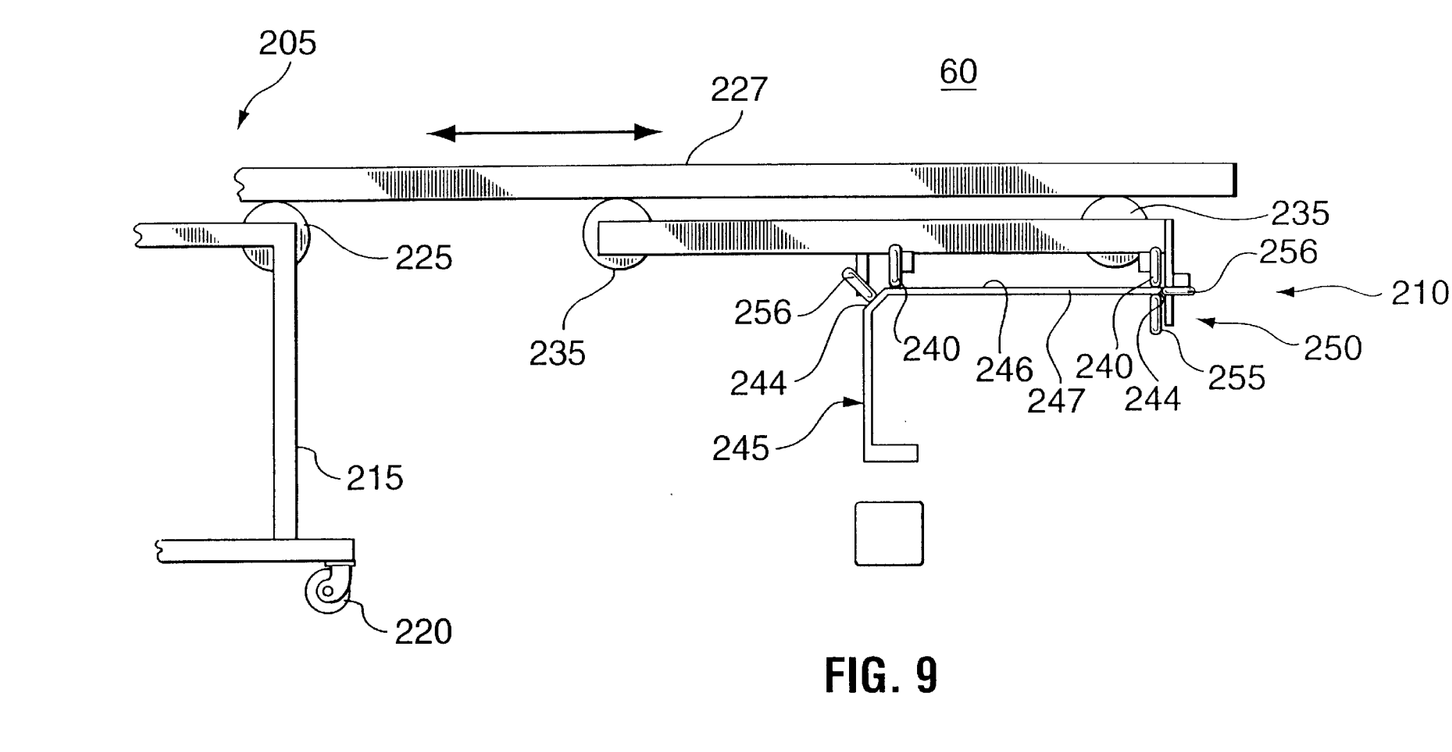
FIG. 9 is a side view of a portion of the patient support apparatus.

Referring to FIGS. 1 to 9, a nuclear camera detector 5 is supported and positioned relative to a patient by a support structure 10. Nuclear camera detectors are heavy, usually weighing approximately three to four thousand pounds. Thus, the support structure 10 should be strong and stable in order to be able to position the camera detector 5 safely and accurately. The support structure 10 includes a base 15, an annular support 20, an elongate support 25, and a guide 30.

The base 15 includes a frame 35. The frame 35 includes twelve lengths of square steel tubing welded together in the shape of a rectangular parallelepiped. The frame 35 has a front square section 37 and a rear square section 38. In the illustrated embodiment, the frame 35 is approximately five feet wide, five feet high, and two feet deep (e.g., approximately 1.5 m wide, 1.5 m high and 0.6 m deep). The frame 35 also includes eight triangular corner braces 40 welded to the front square section 37, that is, each corner of the front square section 37 has two corner braces 40, one towards the front of the front square section 37, and one towards the rear of the front square section 37. In the illustrated embodiment, the corner braces 40 are in the shape of equilateral right angle triangles.

Attached to the underside of the frame 35 are two horizontal legs 45. Attached to each leg 45 are two feet 50. An alternative to the use of feet 50 is to attach the base 15 to a floor by way of bolts set into the floor. The legs 45 extend beyond the frame 35 so as to position the feet 50 wider apart to increase the stability of the base 15. The feet 50 are adjustable so that the base 15 may be levelled. Thus constructed, the base 15 is strong, stable, rigid, and capable of supporting heavy loads.

The annular support 20 is vertically oriented, having an inner surface 55 defining an orifice 60, an outer surface 65, a front surface 70, and a rear surface 75. The annular support 20 is constructed of a ductile iron casting capable of supporting heavy loads. In the illustrated embodiment, the annular support 20 has an outside diameter of about fifty two inches (e.g., about 1.3 m. The annular support 20 is supported by upper rollers 80 and lower rollers 85 which are mounted on the base 15. The upper rollers 80 and lower rollers 85 roll on the outer surface 65, thus enabling the annular support 20 to rotate relative to the base 15 in the plane defined by the annular support 20 (e.g., alternatively referred to as a first plane). Each of the upper rollers 80 and lower rollers 85 are mounted onto a pair of corner braces 40 by way of axles with deep groove bearings. The bearings should be low friction and be able to withstand heavy loads. The axles of the upper rollers 80 are radially adjustable relative to the annular support 20, so that the normal force exerted by the upper rollers 80 on the outer surface 65 is adjustable. The curved surfaces of the upper rollers 80 and lower rollers 85 (i.e. the surfaces that contact the outer surface 65) should be tough so as to be able to withstand the pressures exerted by the annular support 20, and should have a fairly high coefficient of friction so as to roll consistently relative to the annular support 20.

Attached to each pair of corner braces 40 is a stabilizing arm 90 oriented perpendicularly to the plane of the annular support 20. A pair of small stabilizing rollers 95 are mounted onto each stabilizing arm 90. Each pair of stabilizing rollers 95 is positioned such that one stabilizing roller 95 rolls on the front surface 70, and the other stabilizing roller 95 rolls on the rear surface 75. The stabilizing rollers 95 maintain the annular support 20 in the vertical plane.

The elongate support 25 includes a pair of support arms 100, each of which extends through an aperture in the annular support 20. The nuclear camera detector 5 is rotatably attached to one end of the pair of support arms 100, such that the nuclear camera detector 5 faces the front surface 70. A counter weight 105 is attached to the other end of the pair of support arms 100, such that the counterweight 105 faces the rear surface 75.

The counter weight 105 includes a pair of parallel counter weight members 110, each of which is pivotally attached to one of the support arms 100. A first weight 115 is attached to one end of the pair of counter weight members 110, and a second weight 120 is attached to the other end of the pair of counter weight members 110. A pair of counter weight links 121 connect the counter weight members 110 to the annular support 20. Each counter weight link 121 is pivotally attached at one end to its corresponding counter weight member 110. Each counter weight link 121 is pivotally attached at its other end to a counter weight bracket 122 which is rigidly attached to the annular support 20. The counter weight links 121 are attached to the counterweight members 110 and counter weight brackets 122 using bolts and tapered roller bearings. Each counter weight link 121 is pivotable relative to the annular support 20 in a plane perpendicular to and fixed relative to the annular support 20.

The guide 30 attaches the elongate support 25 to the annular support 20, and controls the position of the elongate support 25, and hence the scintillation camera detector 5, relative to the annular support 20. A pair of brackets 125 is rigidly attached to the annular support 20. A pair of rigid links 130 is pivotally attached at support arm pivot points 135 to the support arms 100. The pair of links 130 is also pivotally attached at bracket pivot points 140 to the brackets 125. At the support arm pivot points 135 and bracket pivot points 140 are tapered roller bearings mounted with bolts. Each link 130 is pivotable relative to the annular support 20 in a plane perpendicular to and fixed relative to the annular support 20. Thus, as the annular support 20 rotates relative to the base 15, the respective planes in which each link 130 and each support arm 100 can move remain fixed relative to the annular support 20.

A pair of linear tracks 145 are rigidly attached to the front surface 70 of the annular support 20. The tracks 145 are oriented such that they are parallel to the respective planes in which each link 130 and each support arm 100 can move. A pair of rigid sliding arms 150 (not shown in FIG. 1) include camera ends 155 and straight ends 160. Each camera end 155 is pivotally attached to one of the support arms 100 at the point of attachment of the scintillation camera detector 5. Each straight end 160 includes a pair of spaced apart cam followers or guides 165 slidable within the corresponding track 145. Thus, movement of the scintillation camera detector 5 relative to the annular support 20 (i.e. we are not concerned, at this point, with rotational movement of the scintillation camera detector 5 relative to the elongate support 25) is linear and parallel to the plane of the annular support 20. Note that if the camera ends 155 were pivotally attached to the support arms 100 between the nuclear camera detector 5 and the annular support 20, the movement of the nuclear camera detector 5 relative to the annular support 20 would not be linear.

Movement of the scintillation camera detector 5 relative to the annular support 20 is effected by an actuator 170. The actuator 170 includes a fixed end 175 pivotally attached to the annular support 20, and a movable end 180 pivotally attached to the elongate support 25. The actuator 170 is extendable and retractable, and is thus able to move the elongate support 25 relative to the annular support 20.

Movement of the annular support 20 relative to the base 15 is effected by a drive unit 185. The drive unit 185 includes a quarter horsepower permanent magnet DC motor and a gearbox to reduce the speed of the output shaft of the drive unit 185. Alternatively, other types of motors could be used, such as hydraulic or pneumatic motors. The output shaft of the drive unit 185 is coupled, by means of a toothed timing belt 195 and two pulley wheels 200, to the axle of a drive roller 190, which is simply one of the lower rollers 85, thus driving the drive roller 190. Power is then transferred from the drive roller 190 to the annular support 20 by friction between the drive roller 190 and the outer surface 65 of the annular support 20.

The support structure 10 of the illustrated embodiment is designed to operate with an apparatus for supporting and positioning a patient, such apparatus including a detached patient support 205, an engaged patient support 210, and a cylinder 245.

The detached patient support 205 includes rigid patient frame 215 supported by four casters 220. Mounted near the top of the patient frame 215 are first support wheels 225 for supporting a stretcher 227 upon which a patient is lying. Two parallel, spaced apart side rails 230 are rigidly attached to the patient frame 215. The first support wheels 225 and the side rails 230 are arranged to enable the stretcher 227 to roll lengthwise on the detached patient support 205. Thus, if the patient support 205 faces the front surface 70 such that the patient support is central and perpendicular relative to the annular support 20, the stretcher 227 is movable on the first patient support wheels 225 substantially along the axis of the annular support 20. A gear box and motor unit 237 driving at least one of the first patient support wheels 225 moves the stretcher 227 as described. A 0.125 horsepower permanent magnet DC motor has been found to be adequate.

The detached patient support 205 can be used both for transporting a patient to and from the scintillation camera detector 5 and support structure 10 therefor, and for supporting and positioning a patient relative to the base 15 during operation of the scintillation camera detector 5 and support structure 10. To ensure that the detached patient support 205 remains stationary during operation of the scintillation camera detector 5, four stabilizers 233 can be lowered. Thus lowered, the stabilizers 233 ensure that the detached patient support remains stationary relative to the floor.

The engaged patient support 210 includes second support wheels 235. The second support wheels 235 are positioned such that the stretcher 227 rolled along the first support wheels 225 can roll onto the second support wheels 235 until the stretcher 227 is either fully or partially supported by the second support wheels 235. The engaged patient support 210 also includes four transverse wheels 240.

The cylinder 245 is rigidly mounted to the annular support 20. The cylinder 215 is aligned with the orifice 60 of the annular support 20 such that the cylinder is coaxial with the annular support 20. The cylinder 245 includes a smooth inner surface 246 upon which rest the transverse wheels 240 of the engaged patient support 210. Thus, the arrangement is such that the patient remains stationary substantially along the axis of the annular support 20 as the annular support 20 rotates relative to the base 15, regardless of whether the board or stretcher is supported by the first support wheels 225, the second support wheels 235, or both.

The engaged patient support 210 also includes a stabilizer 250. The stabilizer 250 includes outside wheels 255 to maintain the engaged patient support 210 horizontal, that is, to stop the engaged patient support from tipping relative to the cylinder 245. The outside wheels 255 roll on the outside surface 243 of the cylinder 245. The stabilizer 250 also includes end wheels 256 to prevent the engaged patient support 210 from moving in a direction parallel to the axis of the cylinder 245. The end wheels 256 roll on the ends 244 of the cylinder 245.

Numerous modifications, variations and adaptations may be made to the particular embodiments of the invention described above without departing from the scope of the invention, which is defined in the claims.

I claim:

1. A support structure for supporting and positioning a scintillation camera detector relative to a patient, the support structure comprising:

(a) a base positionable on a ground surface and comprising:
  (i) a pair of spaced apart lower rollers;
  (ii) a pair of spaced apart upper rollers; and
  (iii) a plurality of stabilizing rollers;

(b) a vertically oriented annular rotating support defining an orifice and a first vertical plane and being rotatable in the first vertical plane, the rotating support comprising:
  (i) an outside surface in rolling contact with the lower rollers and upper rollers;
  (ii) an inside surface for supporting a patient support;
  (iii) a front surface in rolling contact with at least one stabilizing roller;
  (iv) a rear surface in rolling contact with at least one stabilizing roller; and
  (v) two spaced apart apertures extending through the front and rear surfaces;

(c) an elongate support comprising a pair of spaced apart arms extending through the apertures in the rotating support, the elongate support comprising:
  (i) a camera end for supporting a scintillation camera detector at a distance from the front surface of the rotating support; and
  (ii) a counter weight end for supporting a counter weight at a distance from the rear surface of the rotating support;

(d) a guiding linkage connecting the rotating support to the elongate support such that pivotal movement of the elongate support relative to the rotating support results in movement of the camera end of the elongate support in a second vertical plane, the guide comprising:
  (i) a pair of rigid links, each link having a rotating support end pivotally attached to the front surface of the rotating support, and an elongate support end pivotally attached to one of the spaced apart arms;
  (ii) a pair of parallel linear tracks attached to the front surface of the rotating support; and
  (iii) a pair of rigid sliding arms, each sliding arm being slidable in respective planes parallel to each other and perpendicular to the rotating support, each sliding arm comprising:
    (a) a track end comprising two spaced apart guides slidable along one of the linear tracks; and
    (b) an elongate support end pivotally attached to one of the spaced apart arms at the camera end;

(e) a counter weight depending from the counter weight end of the elongate support, the counter weight comprising:
  (i) a pair of elongate counter weight members, each counter weight member being pivotally attached to and depending from one of the spaced apart arms and comprising an upper end and a lower end;
  (ii) an upper counter weight spanning the upper ends of the counter weight members;
  (iii) a lower counter weight spanning the lower ends of the counter weight members, the lower counter weight being heavier than the upper counter weight; and
  (iv) a pair of rigid counter weight links, each link having an annular support end pivotally attached to the rear surface of the annular support, and a counter weight end pivotally attached to the lower counter weight;

(f) an actuator for pivoting the elongate member relative to the annular support, the actuator being movable between an extended position and a retracted position, the actuator comprising:
  (i) an annular support end pivotally attached to the annular support; and
  (ii) an elongate support end pivotally attached to the elongate support at a distance from the rear surface of the elongate support;
(g) a drive unit for rotating the annular support relative to the base, the drive unit comprising an electric motor driving one of the lower rollers which then drives the annular support; and
(h) a cylindrical patient support coaxially mounted to the annular support within the orifice defined by the annular support.

2. A support structure for supporting and positioning a device relative to a patient, the support structure comprising:
  a base;
  a rotating support rotatable in a first plane relative to the base;
  an elongate support pivotally attached to the rotating support such that the elongate support is movable in a second plane, the second plane being at an angle to the first plane, the elongate support comprising a device end for supporting the device; and
  a guiding linkage connected to the rotating support for restricting movement of the device end of the elongate support to a third plane, the third plane being substantially perpendicular to the second plane.

3. The support structure as defined in claim 2, wherein the third plane is substantially parallel to the first plane.

4. The support structure as defined in claim 3, wherein the rotating support is annular in shape and vertically oriented, the rotating support is rotatable relative to the base in a vertical plane, and the elongate support extends through the annular rotating support and includes:
  a counter weight end opposite the device end; and
  a pair of spaced apart arms, each arm having a device end and a counter weight end opposite the device end, the device ends being constructed and arranged to support a device therebetween; and the guide comprising a mechanical linkage between the rotatable support and the elongate support, the mechanical linkage effecting rotational movement relative to the base and linear movement of the device end relative to the base, the mechanical linkage comprising:
    a pair of parallel linear tracks attached to a front surface of the rotating support;
    a pair of rigid sliding arms, each sliding arm being slidable in respective planes parallel to each other and perpendicular to the rotating support, each sliding arm comprising:
      a track end comprising two spaced apart guides slidable along one of the linear tracks; and
      an elongate support end pivotally attached to one of the spaced apart arms at the camera end; and
    a pair of rigid links, each link having a rotating support end pivotally attached to the front surface of the rotating support, and an elongate support end pivotally attached to one of the spaced apart arms.

5. The support structure as defined in claim 2, wherein the rotating support is circular in shape and is vertically oriented, the rotating support being rotatable relative to the base in a vertical plane.

6. The support structure as defined in claim 5, wherein the rotating support is annular in shape.

7. The support structure as defined in claim 2, wherein the elongate support extends through the rotating support, the elongate support comprising a counter weight end opposite the device end.

8. The support structure as defined in claim 2, wherein the elongate support comprises a pair of spaced apart arms, each arm comprising a device end and a counter weight end opposite the device end, the device ends being constructed and arranged to support the device therebetween.

9. The support structure as defined in claim 2, the guide comprising:
  a pair of parallel linear tracks attached to the front surface of the rotating support; and
  a pair of rigid sliding arms, each sliding arm being slidable in respective planes parallel to each other and perpendicular to the rotating support, each sliding arm comprising:
    a track end comprising two spaced apart guides slidable along one of the linear tracks; and
    an elongate support end pivotally attached to one of a pair of spaced apart arms at the device end of the elongate support arm.

10. The support structure as defined in claim 2, further comprising a rigid link for pivotally attaching the elongate support to the rotating support at an angle to the first plane, the rigid link comprising a first end pivotally attached to the elongate support, and a second end pivotally attached to the rotating support.

11. The support structure as defined in claim 2, further comprising a rigid link for pivotally attaching the elongate support to the rotating support at an angle to the first plane, the rigid link comprising a first end pivotally attached to the elongate support, and a second end pivotally attached to the rotating support; wherein the guide further comprises:
  a pair of parallel linear tracks attached to the front surface of the rotating support; and
  a pair of rigid sliding arms, each sliding arm being slidable in respective planes parallel to each other and perpendicular to the rotating support, each sliding arm comprising:
    a track end comprising two spaced apart guides slidable along one of the linear tracks; and
    an elongate support end pivotally attached to one of a pair of spaced apart arms at the device end of the elongate support.

12. A support structure for supporting and positioning a device relative to a patient, comprising:
  a base;
  an annular rotating support rotatable in a first plane relative to the base, the rotating support being vertically oriented and rotatable relative to the base in a vertical plane;
  an elongate support comprising:
    a device end for supporting the device;
    a counter weight end opposite the device end; and
    a pair of spaced apart arms, each arm comprising a device end and a counter weight end opposite the device end, the device ends being constructed and arranged to support a device therebetween, and the elongate support being pivotally attached to the rotating support at an angle to the first plane, the elongate support extending through the rotating support;
  a guide for restricting movement of the device end of the elongate support to a second plane fixed relative to the base, the second plane being parallel to the first plane, the guide comprising:
    a pair of parallel linear tracks attached to a front surface of the rotating support; and a pair of rigid sliding arms, each sliding arm being slidable in respective planes parallel to each other and perpendicular to the rotating support, each sliding arm comprising:
a track end comprising two spaced apart guides slidable along one of the linear tracks; and
an elongate support end pivotally attached to one of the spaced apart arms at the device end; and
a rigid link for pivotally attaching the elongate support to the rotating support at an angle to the first plane, the rigid link comprising a first end pivotally attached to the elongate support, and a second end pivotally attached to the rotating support.

13. A support structure for supporting and positioning a scintillation camera detector relative to a patient, comprising:
a base positionable on a ground surface and comprising a pair of spaced apart lower rollers;
a vertically oriented annular rotating support defining an orifice and a first vertical plane and being rotatable in the first vertical plane, the rotating support comprising:
an outside surface in rolling contact with the lower rollers;
an inside surface for supporting a patient support;
a front surface; and
a rear surface;
an elongate support having a pair of spaced apart arms extending through the rotating support, and being pivotally attached to the rotating support such that the elongate support is moveable in a second plane at an angle relative to the first plane, the elongate support including:
a camera end for supporting a scintillation camera detector at a distance from the front surface of the rotating support; and
a counter weight end for supporting a counter weight at a distance from the rear surface of the rotating support;
a guiding linkage connecting the rotating support to the elongate support such that pivotal movement of the elongate support relative to the rotating support results in movement of the camera end of the elongate support in a third vertical plane, the third vertical plane being substantially parallel to the first vertical plane;
a counter weight depending from the counter weight end of the elongate support;
an actuator for pivoting the elongate member relative to the annular support; and
a drive unit for rotating the annular support relative to the base.

14. The support structure as defined in claim 13, wherein the guiding linkage effectuates rotational movement relative to the base and linear movement of the camera end relative to the base.

15. The support structure as defined in claim 14, wherein the guiding linkage comprises:
a pair of parallel linear tracks attached to the front surface of the rotating support; and
a pair of rigid sliding arms, each sliding arm being slidable in respective planes parallel to each other and perpendicular to the rotating support, each sliding arm comprising:
a track end comprising two spaced apart guides slidable along one of the linear tracks; and
an elongate support end pivotally attached to one of the spaced apart arms at the camera end.

16. The support structure as defined in claim 14, wherein the guiding linkage comprises a pair of rigid links, each link having a rotating support end pivotally attached to the front surface of the rotating support, and an elongate support end pivotally attached to one of the spaced apart arms.

17. The support structure as defined in claim 13, wherein the guiding linkage further comprises:
a pair of rigid links, each link having a rotating support end pivotally attached to the front surface of the rotating support, and an elongate support end pivotally attached to one of the spaced apart arms;
a pair of parallel linear tracks attached to the front surface of the rotating support; and
a pair of rigid sliding arms, each sliding arm being slidable in respective planes parallel to each other and perpendicular to the rotating support, each sliding arm comprising:
a track end comprising two spaced apart guides slidable along one of the linear tracks; and
an elongate support end pivotally attached to one of the spaced apart arms at the camera end.

18. The support structure as defined in claim 13, wherein the base further comprises a pair of spaced apart upper rollers in rolling contact with the outside surface of the rotating support, and a plurality of stabilizing rollers in rolling contact with the front and rear surfaces of the rotating support.

19. The support structure as defined in claim 13, wherein the pair of spaced apart arms extend through two apertures in the rotating support.

20. The support structure as defined in claim 13, further comprising a cylindrical patient support coaxially mounted to the annular support within the orifice defined by the annular support.

21. The support structure as defined in claim 13, further comprising means for adjusting the position of a scintillation camera detector relative to the camera end of the elongate support such that the axis of rotation of the scintillation camera detector relative to the camera end of the elongate support is maintainable substantially at the center of gravity of the scintillation camera detector.

22. The support structure as defined in claim 13, further comprising a patient support movable relative to the rotating support and having one end in rolling contact with and supportable by the inside surface of the rotating support.

23. The support structure as defined in claim 13, wherein the counter weight further comprises:
a pair of elongate counter weight members, each counter weight member being pivotally attached to and depending from one of the spaced apart arms of the elongate support and having an upper end and a lower end;
an upper counter weight spanning the upper ends of the counter weight members;
a lower counter weight spanning the lower ends of the counter weight members, the lower counter weight being heavier than the upper counter weight; and
a pair of rigid counter weight links, each link having an annular support end pivotally attached to the rear surface of the annular support, and a counter weight end pivotally attached to the lower counter weight.

24. The support structure as defined in claim 13, wherein the actuator is movable between an extended position and a retracted position and further comprises:
an annular support end pivotally attached to the annular support; and
an elongate support end pivotally attached to the elongate support at a distance from the rear surface of the elongate support.

25. The support structure as defined in claim 13, wherein the drive unit further comprises an electric motor driving one of the lower rollers which then drives the annular support.

26. A support structure for supporting and positioning a device relative to a patient, the support structure comprising:

a base;

a rotating support being circular and annular in shape and vertically oriented, the rotating support being rotatable relative to the base in a first vertical plane;

an elongate support pivotally attached to the rotating support such that the elongate support is movable in a second plane at an angle to the first plane, the elongate support comprising a pair of spaced apart arms, each arm comprising a device end, the device ends being constructed and arranged to support a device therebetween, the elongate support extending through the rotating support, the elongate support comprising a counter weight end opposite the device end;

a guiding linkage connected to the rotating support for restricting movement of the device end of the elongate support to a third plane perpendicular to the second plane; and wherein the third plane is substantially parallel to the first plane.

\* \* \* \* \*